US00PP17539P2

(12) United States Plant Patent
Smith

(10) Patent No.: US PP17,539 P2
(45) Date of Patent: Mar. 27, 2007

(54) ***CHRYSANTHEMUM* PLANT NAMED 'FROSTY YOJEANETTE'**

(50) Latin Name: *Chrysanthemum×morifolium*
Varietal Denomination: Frosty Yojeanette

(75) Inventor: Mark A. Smith, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/212,361

(22) Filed: Aug. 26, 2005

(51) Int. Cl.
*A01H 5/00* (2006.01)

(52) U.S. Cl. ..... Plt./294

(58) Field of Classification Search ..... Plt./294
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Frosty Yojeanette', characterized by its upright and rounded plant habit; freely branching habit; dense and full plants; uniform and freely flowering habit; medium-sized daisy-type inflorescences with elongated oblong-shaped ray florets; white-colored ray florets; and natural season flowering in early October in the Northern Hemisphere.

2 Drawing Sheets

Botanical designation: *Chrysanthemum×morifolium.*
Cultivar denomination: 'Frosty Yojeanette'.

BACKGROUND OF THE INVENTION

The present invention relates to a new and distinct cultivar of *Chrysanthemum* plant, botanically known as *Chrysanthemum×morifolium,* commercially known as a garden-type *Chrysanthemum* and hereinafter referred to by the name 'Frosty Yojeanette'.

The new cultivar is a product of a planned breeding program conducted by the Inventor. The objective of the breeding program is to create new garden-type *Chrysanthemum* cultivars having inflorescences with desirable inflorescence forms, attractive floret colors and good garden performance.

The new *Chrysanthemum* is a naturally-occurring whole plant mutation of the *Chrysanthemum×morifolium* cultivar Sweet Yojeanette, disclosed in U.S. Plant Pat. No. 16,212. The new *Chrysanthemum* was discovered and selected by the Inventor as a single flowering plant from within a population of plants of the cultivar Sweet Yojeanette in a controlled environment in Monroeville, N.J. in October, 2003. The selection of this plant was based on its desirable inflorescence form, attractive ray floret color and good garden performance.

Asexual reproduction of the new cultivar by terminal vegetative cuttings in a controlled environment in Smoketown, Pa. since December, 2003, has shown that the unique features of this new *Chrysanthemum* are stable and reproduced true to type in successive generations.

SUMMARY OF THE INVENTION

The cultivar Frosty Yojeanette has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Frosty Yojeanette'. These characteristics in combination distinguish 'Frosty Yojeanette' as a new and distinct cultivar:

1. Upright and rounded plant habit.
2. Freely branching habit; dense and full plants.
3. Uniform and freely flowering habit.
4. Medium-sized daisy-type inflorescences with elongated oblong-shaped ray florets.
5. White-colored ray florets.
6. Natural season flowering in early October in the Northern Hemisphere.

In side-by-side comparisons conducted in Alva, Fla., plants of the new *Chrysanthemum* differed from plants of the parent, the cultivar Sweet Yojeanette, primarily in ray floret coloration as ray florets of plants of the new *Chrysanthemum* did not "pink" under cool climatic conditions whereas ray florets of plants of the cultivar Sweet Yojeanette did "pink" under cool climatic conditions. In addition, plants of the new *Chrysanthemum* were slightly shorter and flowered one or two days later than plants of the cultivar Sweet Yojeanette when grown under artificial daylength conditions.

Plants of the new *Chrysanthemum* can be compared to plants of the *Chrysanthemum* cultivar Shepherd, disclosed in U.S. Plant Pat. No. 13,371. In side-by-side comparisons conducted in Alva, Fla., plants of the new *Chrysanthemum* differed from plants of the cultivar Shepherd in the following characteristics:

1. Plants of the new *Chrysanthemum* were larger than plants of the cultivar Shepherd.
2. Plants of the new *Chrysanthemum* had smaller inflorescence discs than plants of the cultivar Shepherd.
3. Plants of the new *Chrysanthemum* flowered more uniformly than plants of the cultivar Shepherd.
4. Plants of the new *Chrysanthemum* flowered about five days later than plants of the cultivar Shepherd.

Plants of the new *Chrysanthemum* can also be compared to plants of the *Chrysanthemum* cultivar Angelina, not patented. In side-by-side comparisons conducted in Alva, Fla., plants of the new *Chrysanthemum* differed from plants of the cultivar Angelina in the following characteristics:

1. Plants of the new *Chrysanthemum* were larger than plants of the cultivar Angelina.
2. Plants of the new *Chrysanthemum* had larger inflorescences than plants of the cultivar Angelina.
3. Inflorescences of plants of the new *Chrysanthemum* were longer lasting than inflorescences of plants of the cultivar Angelina.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of a typical flowering plant of 'Frosty Yojeanette' grown in a container.

The photograph on the second sheet comprises a close-up view of typical inflorescences of the cultivar 'Frosty Yojeanette'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the summer in a glass-covered greenhouse and under conditions and practices which approximate those generally used in commercial garden-type *Chrysanthemum* production. Rooted cuttings were planted in 15.25-cm containers, grown under artificial long day conditions (four-hour night interruption) and pinched about ten days later. About ten days after the pinch, plants were then exposed to artificial short day conditions (11.5 hours light) until flowering. During the production of the plants, temperatures ranged from 18° C. to 38° C. Measurements and numerical values represent averages for typical flowering plants.

Botanical classification: *Chrysanthemum×morifolium* cultivar Frosty Yojeanette.

Commercial classification: Daisy-type garden *Chrysanthemum.*

Parentage: Naturally-occurring whole plant mutation of the *Chrysanthemum×morifolium* cultivar Sweet Yojeanette, disclosed in U.S. Plant patent application Ser. No. 10/764,880.

Propagation:

*Type.*—Terminal vegetative cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Plant form/growth habit.*—Perennial herbaceous daisy-type garden *Chrysanthemum.* Inverted triangle with mounded crown. Stems initially upright, then somewhat outwardly spreading; rounded growth habit. Freely branching with about seven primary branches with secondary lateral branches potentially forming at every node. Moderately vigorous.

*Plant height.*—About 20.5 cm.

*Plant diameter.*—About 28 cm.

*Lateral branches.*—Length: About 17 cm. Diameter: About 5 mm. Internode length: About 1.3 cm. Aspect: Upright and somewhat outwardly spreading. Texture: Pubescent. Color: 144A.

*Foliage description.*—Leaf arrangement: Alternate. Length: About 3 cm. Width: About 2.4 cm. Apex: Cuspidate. Base: Mostly truncate with attenuate tendencies. Margin: Palmately lobed, sinuses parallel to divergent. Texture, upper surface: Slightly pubescent. Texture, lower surface: Pubescent; veins prominent. Color: Developing and fully expanded foliage, upper surface: More green than 147A. Developing and fully expanded foliage, lower surface: Close to 147B. Venation, upper surface: More green than 147A. Venation, lower surface: Close to 147B. Petiole length: About 1 cm. Petiole diameter: About 2 mm. Petiole color, upper and lower surfaces: Close to 147B.

Inflorescence description:

*Appearance.*—Daisy-type inflorescence form with elongated oblong-shaped ray florets. Inflorescences borne on terminals above foliage, arising from leaf axils. Ray florets developing acropetally on a capitulum. Freely flowering habit with about nine inflorescences per secondary lateral branch.

*Flowering response.*—Under natural season conditions, plants flower in early October in the Northern Hemisphere.

*Inflorescence bud (before showing color).*—Height: About 5 mm. Diameter: About 6 mm. Shape: Oblate. Color (lower surface of phyllaries): Close to 146A to more green than 147A.

*Inflorescence size.*—Diameter: About 3.3 cm. Depth (height): About 1.2 cm. Disc diameter: About 7 mm. Receptacle diameter: About 4 mm.

*Ray florets.*—Shape: Elongated oblong-shaped. Length: About 1.6 cm. Width: About 5 mm. Corolla tube length: About 3 mm. Corolla tube diameter: About 1.5 mm. Apex: Acute, emarginate or rounded. Margin: Fused. Texture, upper and lower surfaces: Smooth, glabrous; satiny. Orientation: Initially upright, then about 80° from vertical. Number of ray florets per inflorescence: About 22 in a single whorl. Color: When opening and fully opened, upper surface: Close to 155D. When opening and fully opened, lower surface: Close to 155D.

*Disc florets.*—Shape: Tubular, elongated. Length: About 3 mm. Width, apex: About 1 mm. Width, base: About 1 mm. Number of disc florets per inflorescence: About 68. Color: Immature: Close to 9A. Mature: Apex: Close to 9A. Mid-section: Close to 154D. Base: Close to 155D.

*Phyllaries.*—Quantity per inflorescence: About 18. Length: About 4 mm. Width: About 2 mm. Shape: Ligulate. Apex: Acute. Base: Truncate. Margin: Entire. Texture, upper surface: Smooth, waxy. Texture, lower surface: Pubescent. Color, upper surface: Close to 146A. Color, lower surface: Close to 146A to more green than 147A.

*Peduncle.*—Length: First peduncle: About 2.4 cm. Fourth peduncle: About 3.3 cm. Diameter: About 1 mm. Strength: Strong. Aspect: About 40° from vertical. Texture: Pubescent. Color: Close to 144A.

*Reproductive organs.*—Androecium: Present on disc florets only. Anther length: Less than 1 mm. Anther color: Close to 12A. Amount of pollen: None observed. Gynoecium: Present on both ray and disc florets. Style length: About 3 mm. Style color: Close to 154A. Stigma color: Close to 9A.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be tolerant to rain, wind and temperatures ranging from 0° C. to more than 38° C.

It is claimed:

1. A new and distinct cultivar of *Chrysanthemum* plant named 'Frosty Yojeanette', as illustrated and described.

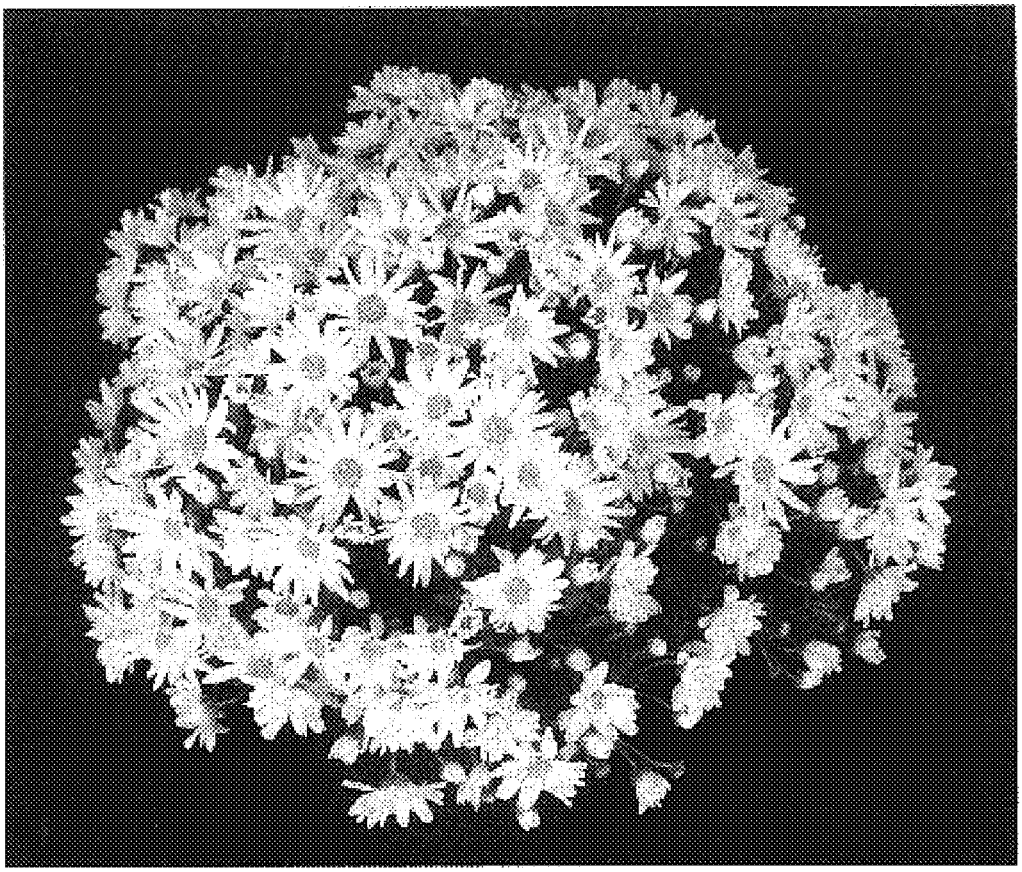

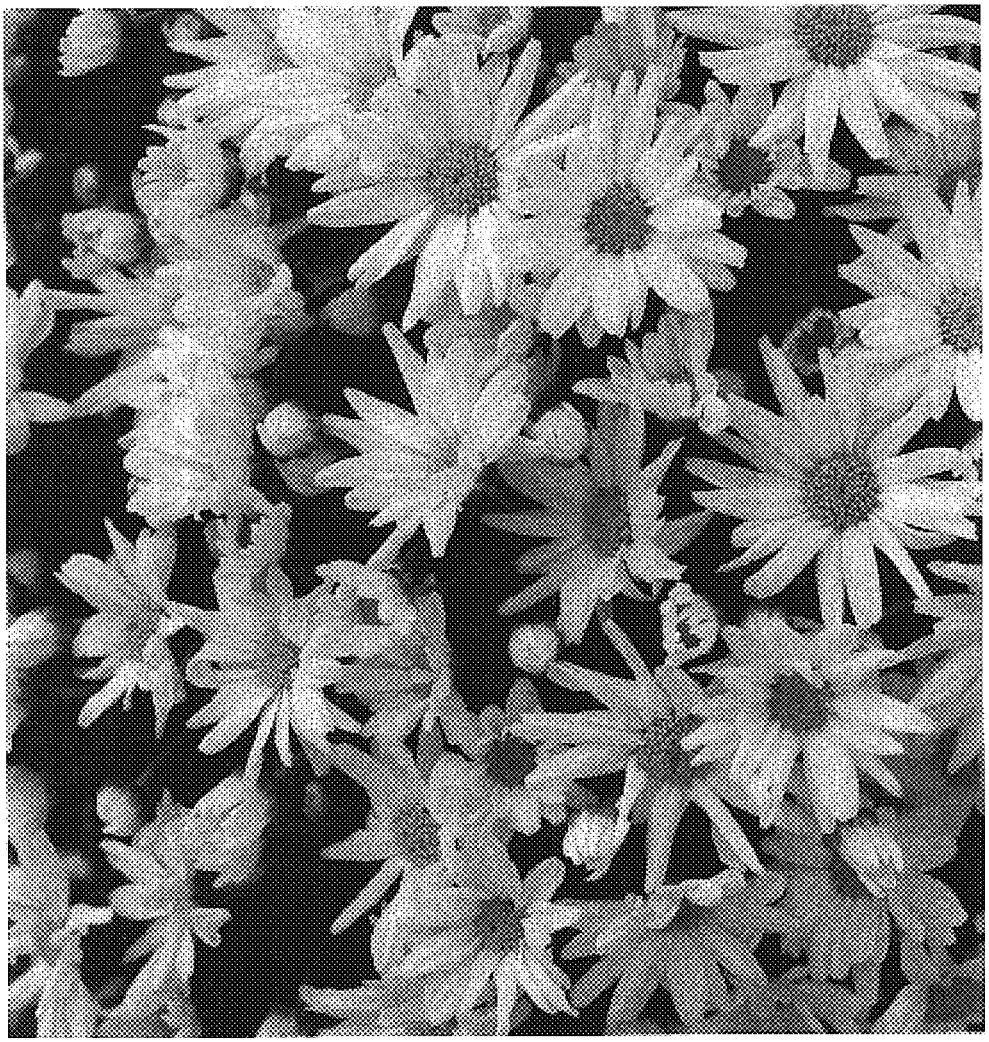

* * * * *